United States Patent
Cox

(10) Patent No.: US 8,175,715 B1
(45) Date of Patent: *May 8, 2012

(54) FREQUENCY AGILE TELEMETRY SYSTEM FOR IMPLANTABLE MEDICAL DEVICE

(75) Inventor: Timothy J. Cox, Friendswood, TX (US)

(73) Assignee: Pacesetter, Inc., Sylmar, CA (US)

( * ) Notice: Subject to any disclaimer, the term of this patent is extended or adjusted under 35 U.S.C. 154(b) by 1132 days.

This patent is subject to a terminal disclaimer.

(21) Appl. No.: 11/613,311

(22) Filed: Dec. 20, 2006

Related U.S. Application Data

(63) Continuation of application No. 10/833,596, filed on Apr. 27, 2004, now Pat. No. 7,177,700, which is a continuation of application No. 10/001,225, filed on Nov. 2, 2001, now Pat. No. 6,763,269.

(51) Int. Cl.
*A61N 1/00* (2006.01)

(52) U.S. Cl. .................. 607/60; 607/9; 607/59; 607/30; 607/32

(58) Field of Classification Search .................... 607/59, 607/60, 9, 30, 32
See application file for complete search history.

(56) References Cited

U.S. PATENT DOCUMENTS

| | | | |
|---|---|---|---|
| 4,561,443 A | 12/1985 | Hogrefe et al. |
| 4,681,111 A | 7/1987 | Silvian |
| 5,058,581 A | 10/1991 | Silvian |
| 5,113,869 A | 5/1992 | Nappholz et al. |
| 5,342,408 A | 8/1994 | deCoriolis et al. |
| 5,354,319 A | 10/1994 | Wyborny et al. |
| 5,381,798 A | 1/1995 | Burrows |
| 5,438,329 A | 8/1995 | Gastouniotis et al. |
| 5,454,838 A | 10/1995 | Vallana et al. |
| 5,496,351 A | 3/1996 | Plicchi et al. |
| 5,496,361 A | 3/1996 | Moberg et al. |
| 5,511,553 A | 4/1996 | Segalowitz |
| 5,518,001 A | 5/1996 | Snell |
| 5,544,661 A | 8/1996 | Davis et al. |
| 5,562,713 A | 10/1996 | Silvian |
| 5,617,871 A | 4/1997 | Burrows |
| 5,626,630 A | 5/1997 | Markowitz et al. |
| 5,674,249 A | 10/1997 | de Coriolis et al. |
| 5,683,432 A | 11/1997 | Goedeke et al. |
| 5,697,958 A | 12/1997 | Paul et al. |
| 5,720,770 A | 2/1998 | Nappholz et al. |
| 5,748,103 A | 5/1998 | Flach et al. |
| 5,752,976 A | 5/1998 | Duffin et al. |
| 5,843,139 A | 12/1998 | Goedeke et al. |
| 5,855,550 A | 1/1999 | Lai et al. |
| 5,861,019 A | 1/1999 | Sun et al. |
| 5,904,708 A | 5/1999 | Goedeke |
| 5,944,659 A | 8/1999 | Flach et al. |
| 5,999,848 A | 12/1999 | Gord et al. |
| 6,004,276 A | 12/1999 | Wright et al. |
| 6,009,350 A | 12/1999 | Renken |
| 6,083,248 A | 7/2000 | Thompson |
| 6,115,636 A | 9/2000 | Ryan |

(Continued)

OTHER PUBLICATIONS

NonFinal Office Action, mailed Dec. 31, 2003: Related U.S. Appl. No. 10/001,225.

(Continued)

*Primary Examiner* — Nicole F Lavert

(57) ABSTRACT

A system enables high-frequency communication between an external communication device and one or more implantable medical devices. The system implements a communication protocol in which the external communication device interrogates any implantable medical devices within range to establish one-to-one communication links for purposes of exchanging data and/or programming the medical devices.

22 Claims, 10 Drawing Sheets

U.S. PATENT DOCUMENTS

| | | | |
|---|---|---|---|
| 6,155,267 | A | 12/2000 | Nelson |
| 6,162,180 | A | 12/2000 | Miesel et al. |
| 6,200,265 | B1 | 3/2001 | Walsh et al. |
| 6,213,942 | B1 | 4/2001 | Flach et al. |
| 6,225,901 | B1 | 5/2001 | Kail, IV |
| 6,230,049 | B1 | 5/2001 | Fischell et al. |
| 6,234,973 | B1 | 5/2001 | Meador et al. |
| 6,238,492 | B1 | 5/2001 | Nakanishi et al. |
| 6,240,317 | B1 | 5/2001 | Villaseca et al. |
| 6,264,614 | B1 | 7/2001 | Albert et al. |
| 6,270,457 | B1 | 8/2001 | Bardy |
| 6,282,441 | B1 | 8/2001 | Raymond et al. |
| 6,301,504 | B1 | 10/2001 | Silvian |
| 6,312,378 | B1 | 11/2001 | Bardy |
| 6,315,721 | B2 | 11/2001 | Schulman et al. |
| 6,418,346 | B1 | 7/2002 | Nelson et al. |
| 6,442,432 | B2 * | 8/2002 | Lee .................... 607/59 |
| 6,480,745 | B2 | 11/2002 | Nelson et al. |
| 6,519,241 | B1 | 2/2003 | Theimer |
| 6,574,511 | B2 | 6/2003 | Lee |
| 6,577,901 | B2 | 6/2003 | Thompson |
| 6,622,050 | B2 * | 9/2003 | Thompson ................ 607/60 |
| 6,763,269 | B2 | 7/2004 | Cox |
| 7,177,700 | B1 | 2/2007 | Cox |
| 2002/0026223 | A1 | 2/2002 | Riff et al. |
| 2002/0123672 | A1 | 9/2002 | Christophersom et al. |

OTHER PUBLICATIONS

Notice of Allowance, mailed Apr. 7, 2004: Related U.S. Appl. No. 10/001,225.

NonFinal Office Action, mailed Jun. 13, 2006: Related U.S. Appl. No. 10/833,596.

Notice of Allowance, mailed Sep. 28, 2006: Related U.S. Appl. No. 10/833,596.

* cited by examiner

FREQUENCY AGILE TELEMETRY SYSTEM FOR IMPLANTABLE MEDICAL DEVICE

CROSS-REFERENCE TO RELATED APPLICATIONS

This application is a continuation of U.S. patent application Ser. No. 10/833,596, filed Apr. 27, 2004, now U.S. Pat. No. 7,177,700, issued on Feb. 13, 2007, which is a continuation of U.S. patent application Ser. No. 10/001,225, filed Nov. 2, 2001, and now U.S. Pat. No. 6,763,269, issued Jul. 13, 2004.

TECHNICAL FIELD

The present invention generally relates to implantable medical devices.

BACKGROUND

There are many kinds of implantable medical devices. Some monitor patient conditions while others disperse some form of therapy. One particular type of implantable medical device is an implantable cardiac therapy device, or ICTD. ICTDs are implanted within the body of a patient to monitor, regulate, and/or correct heart activity. ICTDs include implantable cardiac stimulation devices (e.g., implantable cardiac pacemakers, implantable defibrillators) that apply stimulation therapy to the heart as well as implantable cardiac monitors that monitor heart activity.

ICTDs typically include a control unit positioned within a casing that is implanted into the body and a set of leads that are positioned to impart stimulation and/or monitor cardiac activity. With improved processor and memory technologies, the control units have become increasingly more sophisticated, allowing them to monitor many types of conditions and apply tailored stimulation therapies in response to those conditions.

ICTDs are typically capable of being programmed remotely by an external programming device, often called a "programmer". Today, individual ICTDs are equipped with telemetry circuits that communicate with the programmer. One type of programmer utilizes an electromagnetic wand that is placed near the implanted cardiac device to communicate with the implanted device. The wand contains a coil that forms a transformer coupling with the ICTD telemetry circuitry. The wand transmits low frequency signals by varying the current in a coil.

Early telemetry systems were passive, meaning that the communication was unidirectional from the programmer to the implanted device. Passive telemetry allowed a treating physician to download instructions to the implanted device following implantation. Due to power and size constraints, early commercial versions of the implanted devices were incapable of transmitting information back to the programmer.

As power capabilities improved, active telemetry became feasible, allowing synchronous bi-directional communication between the implanted device and the programmer. Active telemetry utilizes a half-duplex communication mode in which the programmer sends instructions in a predefined frame format and, following termination of this transmission, the implanted device returns data using the frame format. With active telemetry, the treating physician is able to not only program the implanted device, but also retrieve information from the implanted device to evaluate heart activity and device performance. The treating physician may periodically want to review device performance or heart activity data for predefined periods of time to ensure that the device is providing therapy in desired manner. Consequently, current generation implantable cardiac therapy devices incorporate memories, and the processors periodically sample and record various performance parameter measurements in the memories.

Current telemetry systems have a limited communication range between the programmer wand and the ICTD, which is often referred to as "short-range telemetry" or "wand telemetry". For effective communication, the wand is held within two feet of the ICTD, and typically within several inches. One problem is that the ICTD has insufficient power to transmit longer range signals. Another consideration is the inherent EMI-resistant design of the ICTD. The ICTD circuitry is typically housed in a hermetically shielded can to prevent electromagnetic interference (EMI) from disrupting operation. The can prevents penetration of high frequencies, thereby limiting communication to the low frequency range of less than 200 KHz. In one exemplary system, signals sent from the programmer to the implanted device are transmitted on a carrier of approximately 36 KHz, and data is transmitted to and from the implanted device at approximately 8 KBaud.

Conventionally, data about a patient's cardiac condition is gathered and stored by the programmer during programming sessions of the ICTDs. Analysis of the cardiac condition is performed locally by the programming software. Programmers offer comprehensive diagnostic capabilities, high-speed processing, and easy operation, thereby facilitating efficient programming and timely patient follow-up.

In addition to local analysis, TransTelephonic Monitoring (TTM) systems are employed to gather current cardiac data of patients when the patient is remote from the healthcare provider. TTM systems are placed in patients' homes. They typically include a base unit that gathers information from the ICTD much like the programmer would. The base unit is connected to a telephone line so that data may be transmitted to the medical staff responsible for that patient. An example of an ICTD TTM system is a service from St. Jude Medical® and Raytel® Cardiac Services called "Housecall™." This service provides current programmed parameters and episode diagnostic information for a plurality of events including stored electrograms (EGMs). Real-time EGMs with annotated status information can also be transmitted.

Using a telephone and a transmitter, the TTM system provides both the medical staff and the patient the convenience of instant analysis of therapy without having the patient leave the comfort of home. Typically, real-time measurements are transmitted in just minutes. Patients may be closely monitored, and the medical staff has more control of their patient's treatment, thus administering better patient management.

While strides have been made for improving patient monitoring, there remains an ongoing need to improve the communication capabilities between implanted devices and external devices, particularly the need to communicate more effectively over greater transmissions ranges.

SUMMARY

A system enables high-frequency communication between an external communication device and one or more implantable medical devices. The system implements a communication protocol in which the external communication device interrogates any implantable medical devices within range to establish one-to-one communication links for purposes of exchanging data and/or programming the medical devices.

In one implementation, the external communication device transmits an interrogation signal on one or more frequencies within a first set of frequencies. The interrogation signal serves as an invitation to communicate with the implantable medical device. The implantable medical device listens for the interrogation signal at a frequency within the first set of frequencies. Upon receipt, the implantable medical device transmits a reply on a second frequency selected from a second set of frequencies. The first and second set of frequencies may overlap or be mutually exclusive. The external communication device monitors the second set of frequencies for the reply. Upon receipt of the reply, the external communication device assigns a communication channel to the implantable medical device for purposes of continuing communication. For that point, the devices can frequency hop among multiple channels more than once during communication of information.

BRIEF DESCRIPTION OF THE DRAWINGS

In the description that follows, like numerals or reference designators are used to reference like parts or elements.

DETAILED DESCRIPTION

The following discussion unfolds in the context of an implantable cardiac therapy device (ICTD) linked to a networked system of computing systems. It is noted that the ICTD is just one exemplary type of implantable medical device. Other types of implantable medical devices may be employed, such as implantable medicine dispensers, implantable nerve stimulators, and so on.

Cardiac Therapy Network

Figure 1:
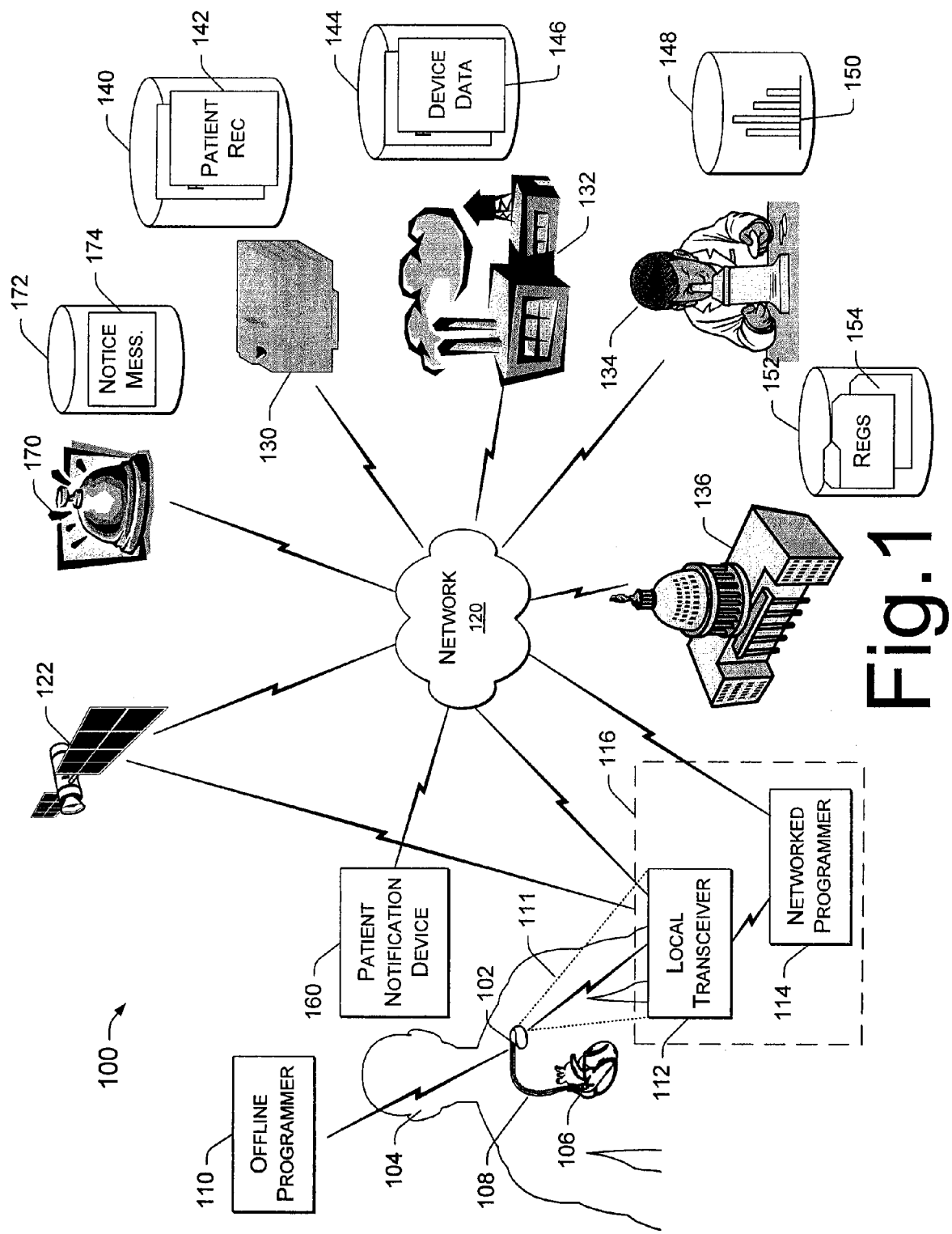
FIG. 1 is a diagrammatic illustration of a network architecture with an exemplary implantable medical device connected to a network of computing systems used by various knowledge workers. The implantable medical device is depicted and described in the context of an implantable cardiac therapy device (ICTD).

FIG. 1 shows an exemplary cardiac therapy network architecture 100 that includes an implantable medical device in the form of an implantable cardiac therapy device (ICTD) 102. The ICTD 102 is coupled to a network of computing systems associated with various knowledge workers who have interest in cardiac therapy. The ICTD is illustrated as being implanted in a human patient 104. The ICTD 102 is in electrical communication with a patient's heart 106 by way of multiple leads 108 suitable for monitoring cardiac activity and/or delivering multi-chamber stimulation and shock therapy.

The ICTD 102 may communicate with a standalone or offline programmer 110 via short-range telemetry technology. The offline programmer 110 is equipped with a wand that, when positioned proximal to the ICTD 102, communicates with the ICTD 102 through a magnetic coupling.

The ICTD 102 can alternatively, or additionally, communicate with a local transceiver 112. The local transceiver 112 may be a device that resides on or near the patient, such as an electronic communications device that is worn by the patient or is situated on a structure within the room or residence of the patient. The local transceiver 112 communicates with the ICTD 102 using short-range telemetry or longer-range high-frequency-based telemetry, such as RF (radio frequency) transmissions. Alternatively, the local transceiver 112 may be incorporated into the ICTD 102, as represented by dashed line 111. In this case, the ICTD includes a separate and isolated package area that accommodates high-frequency transmissions without disrupting operation of the monitoring and stimulation circuitry.

Depending upon the implementation and transmission range, the local transceiver 112 can be in communication with various other devices of the network architecture 100. One possible implementation is for the local transceiver 112 to transmit information received from the ICTD 102 to a networked programmer 114, which is connected to network 120. The networked programmer 114 is similar in operation to standalone programmer 110, but differs in that it is connected to the network 120. The networked programmer 114 may be local to, or remote from, the local transceiver 112; or alternatively, the local transceiver 112 may be incorporated into the networked programmer 114, as represented by dashed line 116.

Another possible implementation is for the local transceiver to be connected directly to the network 120 for communication with remote computing devices and/or programmers. Still another possibility is for the local transceiver 112 to communicate with the network 120 via wireless communication, such as via a satellite system 122.

The network 120 may be implemented by one or more different types of networks (e.g., Internet, local area network, wide area network, telephone, cable, satellite, etc.), including wire-based technologies (e.g., telephone line, cable, fiber optics, etc.) and/or wireless technologies (e.g., RF, cellular, microwave, IR, wireless personal area network, etc.). The network 120 can be configured to support any number of different protocols, including HTTP (HyperText Transport Protocol), TCP/IP (Transmission Control Protocol/Internet Protocol), WAP (Wireless Application Protocol), IEEE 802.11, Bluetooth, and so on.

A number of knowledge workers are interested in data gathered from the implantable cardiac therapy device 102. Representative knowledge workers include healthcare providers 130, the device manufacturer 132, clinical groups 134, and regulatory agencies 136. The knowledge workers are interested in different portions of the data. For instance, the healthcare providers 130 are interested in information pertaining to a particular patient's condition. The manufacturer 132 cares about how the device is operating. The clinical groups 134 want certain data for inclusion in patient populations that can be studied and analyzed. The regulatory agencies 136 are concerned whether the devices, and various treatments administered by them, are safe or pose a health risk.

The network architecture 100 facilitates distribution of the device data to the various knowledge workers. Information gathered from the device is integrated, processed, and distributed to the knowledge workers. Computer systems maintain and store the device data, and prepare the data for efficient presentation to the knowledge workers. The computer systems are represented pictorially in FIG. 1 as databases. However, such systems can be implemented using a wide variety of computing devices, ranging from small handheld computers or portable digital assistants (PDAs) carried by physicians to workstations or mainframe computers with large storage capabilities. The healthcare providers 130 are equipped with computer systems 140 that store and process patient records 142. The manufacturer 132 has a computer system 144 that tracks device data 146 returned from ICTDs 102. The clinical groups 134 have computer systems 148 that store and analyze data across patient populations, as represented by a histogram 150. The regulatory agencies 136 maintain computer systems 152 that register and track healthcare risk data 154 for ICTDs.

The network architecture 100 supports two-way communication. Not only is data collected from the ICTD 102 and distributed to the various computer systems of the knowledge workers, but also information can be returned from these computer systems to the networked programmer 114 and/or the local transceiver 112 for communication back to the ICTD 102. Information returned to the ICTD 102 may be used to adjust operation of the device, or modify therapies being applied by the device. Such information may be imparted to the ICTD 102 automatically, without the patient's knowledge.

Additionally, information may be sent to a patient notification device 160 to notify the patient of some event or item. The patient notification device 160 can be implemented in a number of ways including, for example, as a telephone, a cellular phone, a pager, a PDA (personal digital assistant), a dedicated patient communication device, a computer, an alarm, and so on. Notifications may be as simple as an instruction to sound an alarm to inform the patient to call into the healthcare providers, or as complex as HTML-based pages with graphics and textual data to educate the patient. Notification messages sent to the patient notification device 160 can contain essentially any type of information related to cardiac medicinal purposes or device operation. Such information might include new studies released by clinical groups pertaining to device operation and patient activity (e.g., habits, diets, exercise, etc.), recall notices or operational data from the manufacturer, patient-specific instructions sent by the healthcare providers, or warnings published by regulatory groups.

Notifications can be sent directly from the knowledge worker to the patient. Additionally, the network architecture 100 may include a notification system 170 that operates computer systems 172 designed to create and deliver notification messages 174 on behalf of the knowledge workers. The notification system 170 delivers the messages in formats supported by the various types of patient notification devices 160. For instance, if the patient carries a pager, a notification message might consist of a simple text statement in a pager protocol. For a more sophisticated wireless-enabled PDA or Internet-oriented cellular phone, messages might contain more than text data and be formatted using WAP formats.

Figure 2:
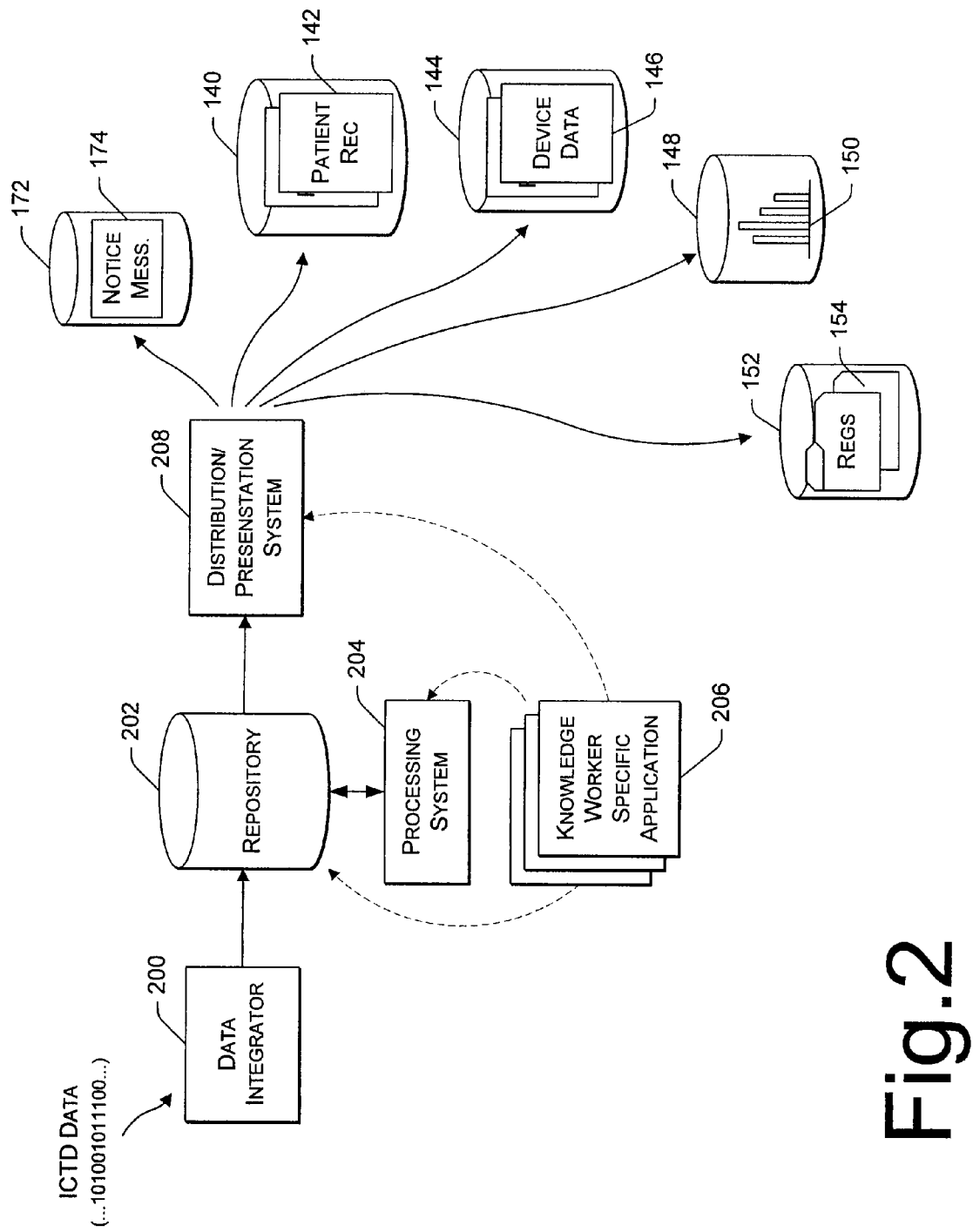
FIG. 2 is a functional diagram illustrating information flow from the ICTD to the computing systems associated with the knowledge workers.

FIG. 2 shows the flow of data from the implantable cardiac therapy device 102 to the various computer systems used by the knowledge workers. Data from the ICTD is output as digital data, as represented by the string of 0's and 1's. The data may consist of any number of items, including heart activity (e.g., ECG), patient information, device operation, analysis results from on-device diagnostics, and so on.

A data integrator 200 accumulates the data and stores it in a repository 202. A processing system 204 processes portions of the data according to various applications 206 that are specifically tailored to place the data into condition for various knowledge workers. For example, healthcare workers might be interested in certain portions of the data, such as the ECG data and the patient information. Clinical scientists might be interested in the heart data, but do not wish to see any patient information. Manufacturers may be interested in the raw data stream itself as a tool to discern how the device is operating. Depending on the needs of the end worker, the processing system 204 takes the raw device data, evaluates its accuracy and completeness, and generates different packages of data for delivery to the various knowledge workers. The processed data packages are also stored in the repository 202.

When the data is ready for delivery, a distribution/presentation system 208 distributes the different packages to the appropriate computer systems 140, 144, 148, 152, and 172. The distribution/presentation system 208 is configured to serve the packages according to the protocols and formats desired by the computer systems. In this manner, the network architecture 100 allows relevant portions of device data, collected from the ICTD, to be disseminated to the appropriate knowledge workers in a form they prefer.

Once the ICTD data is delivered, the computer systems 140, 144, 148, 152, and 172 store the data and/or present the data to the knowledge worker. The computer systems may perform further processing specific to their use of the data. Through these processes, the knowledge workers create additional information that is useful to the patient, or other knowledge workers with interests in ICTDs. For example, from the ICTD data, the knowledge workers might devise improved therapies for a given patient, or create instructions to modify operation of a specific ICTD, or gain a better understanding of how implantable cardiac devices operate in general, or develop better technologies for future generations of ICTDs. Much of this created knowledge can be shared among the various knowledge workers.

Figure 3:
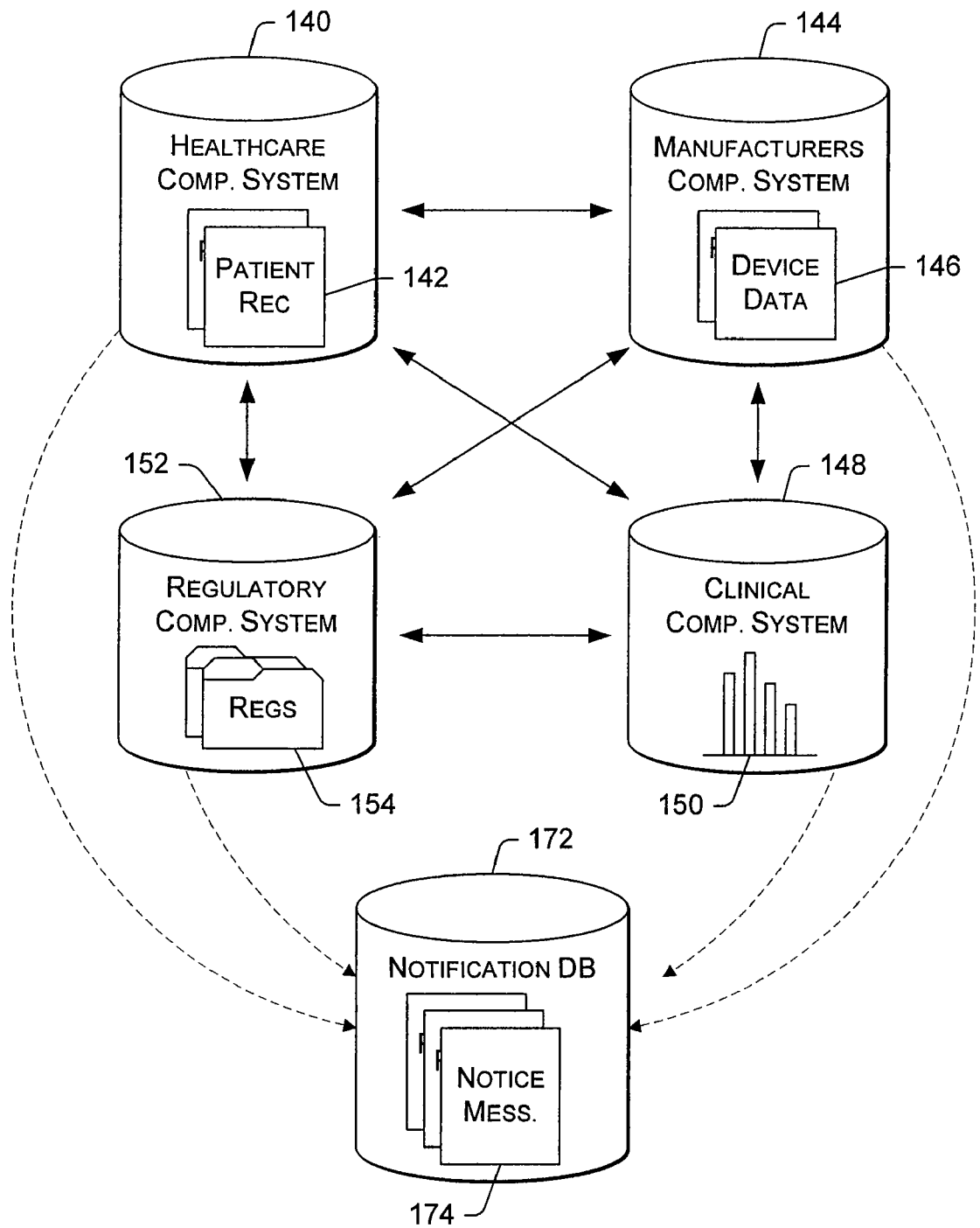
FIG. 3 is a functional diagram illustrating how the various computing systems share pieces of information to improve care given to the patient.

FIG. 3 shows how the various computing systems 140, 144, 148, 152, and 172 can cooperate and share pieces of information to improve the care given to a patient. Where appropriate and legally acceptable, the computer systems may be configured to pass non-private information among the various knowledge workers to better improve their understanding of the implantable medical field. Clinical results 150 produced by the clinical computer systems 148 may be shared with healthcare providers to improve patient care or with manufacturers to help in their design of next generation devices. The sharing of information may further lead to better and timelier healthcare for the patients.

If the collective knowledge base produces information that may prove helpful to the patient, that information can be passed to the notification system 172 for delivery to one or more patients. Also, any one of the knowledge workers may wish to employ the notification system 172 to send messages to the patient(s).

Figure 4:
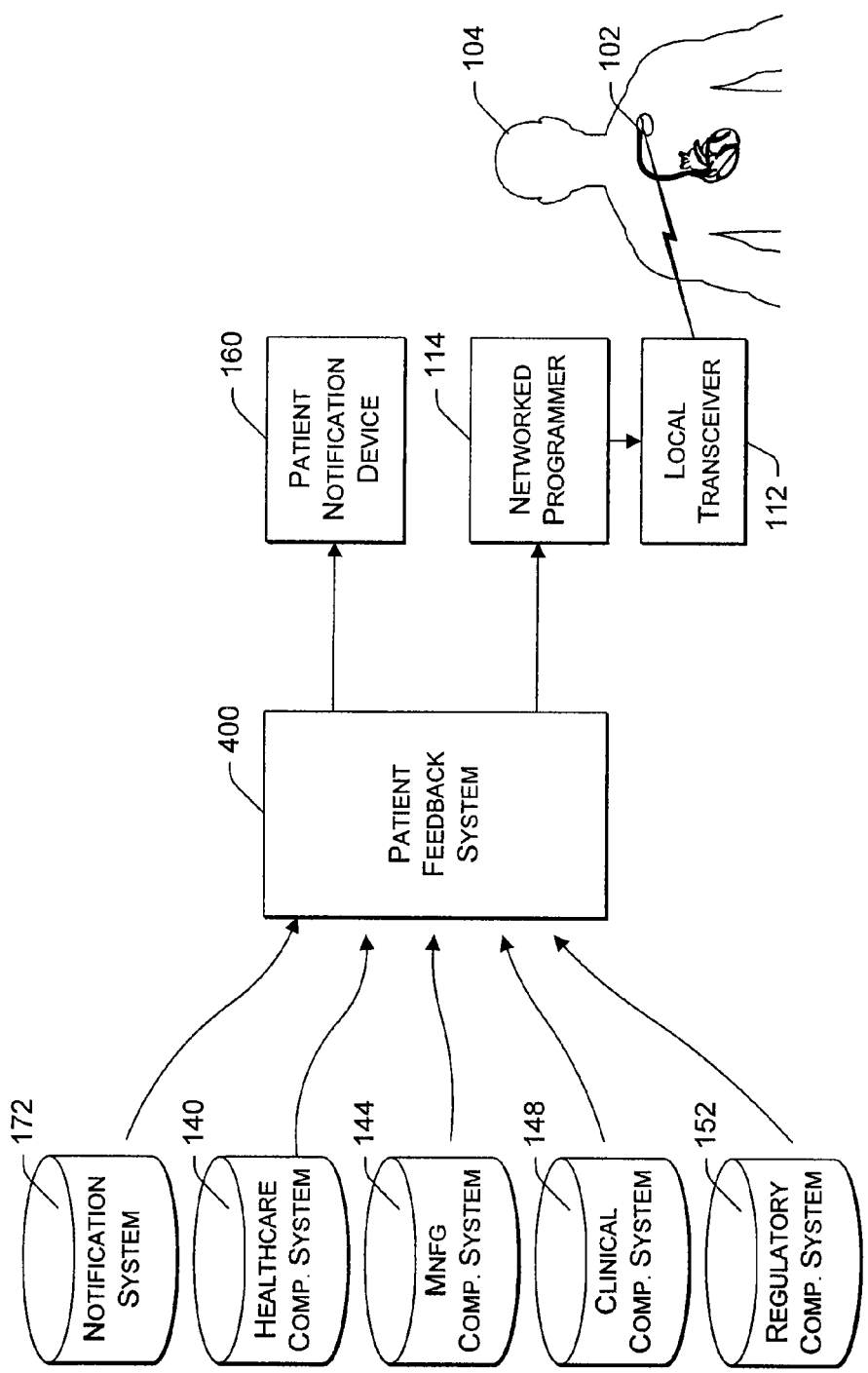
FIG. 4 is a functional diagram illustrating information flow from the computing systems back to the ICTD.

FIG. 4 shows, in more detail, the flow of information back from the various computer systems used by the knowledge workers to the implantable cardiac therapy device 102 or the patient notification device 160. Information from any one of the computing systems—healthcare computer system(s) 140, manufacturer computer system(s) 144, clinical computer system(s) 148, regulatory computer system(s) 152—or the notification system 172 can be sent to a patient feedback system 400. The patient feedback system 400 facilitates delivery of the information back to the patient. It may be an independent system, or incorporated into one or more of the computing systems. It may alternatively be integrated into the notification system 172.

The patient feedback system 400 may be implemented in many ways. As one exemplary implementation, the patient feedback system 400 is implemented as a server that serves content back to the networked programmer 114, which then uses the information to program the ICTD 102 through a built in transceiver 116, local transceiver 112, or wand-based telemetry. As another possible implementation, the patient feedback system may be a cellular or RF transmission system that sends information back to the patient feedback device 160.

The network architecture 100 facilitates continuous care around the clock, regardless of where the patient is located. For instance, suppose the patient is driving in the car when a cardiac episode occurs. The ICTD 102 detects the condition and transmits an alert message about the condition to the local transceiver 112. The message is processed and delivered to a physician's computer or PDA via the network 120. The physician can make a diagnosis and send some instructions back to the patient's ICTD. The physician might also have a notification message that guides the patient to a nearest healthcare facility for further treatment sent via the notification system 170 to the patient's notification device 160. Concurrently, the physician can share the patient's records online with an attending physician at the healthcare facility so that the attending physician can review the records prior to the patient's arrival.

Exemplary ICTD

Figure 5:
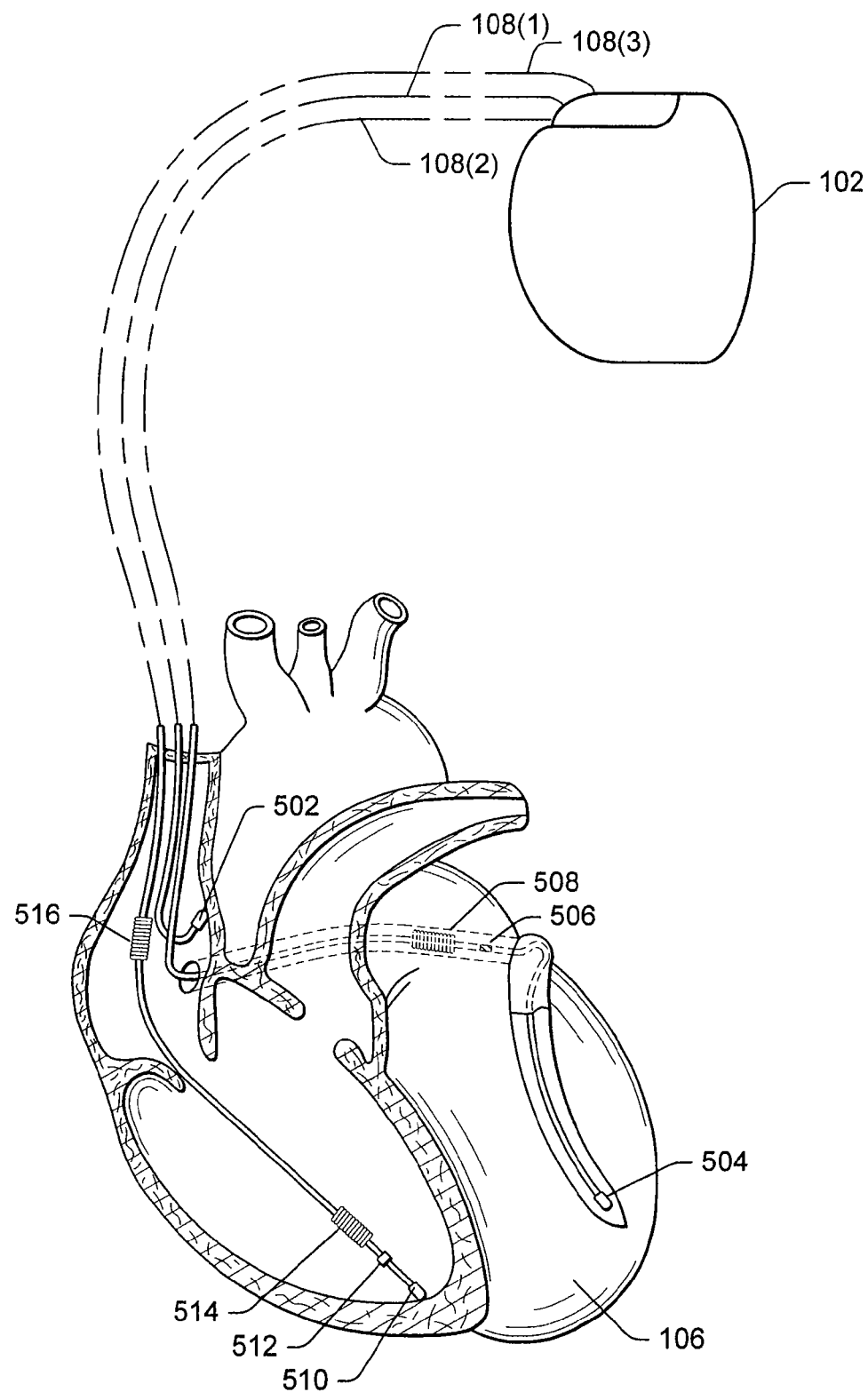
FIG. 5 is a simplified illustration of an ICTD in electrical communication with a patient's heart for monitoring heart activity and/or delivering stimulation therapy.

FIG. 5 shows an exemplary ICTD 102 in electrical communication with a patient's heart 106 for monitoring heart activity and/or delivering stimulation therapy, such as pacing or defibrillation therapies. The ICTD 102 is in electrical communication with a patient's heart 106 by way of three leads 108(1)-(3). To sense atrial cardiac signals and to provide right atrial chamber stimulation therapy, the ICTD 102 is coupled to an implantable right atrial lead 108(1) having at least an atrial tip electrode 502, which typically is implanted in the patient's right atrial appendage. To sense left atrial and ventricular cardiac signals and to provide left chamber pacing therapy, the ICTD 102 is coupled to a coronary sinus lead 108(2) designed for placement in the coronary sinus region via the coronary sinus. The coronary sinus lead 108(2) positions a distal electrode adjacent to the left ventricle and/or additional electrode(s) adjacent to the left atrium. An exemplary coronary sinus lead 108(2) is designed to receive atrial and ventricular cardiac signals and to deliver left ventricular pacing therapy using at least a left ventricular tip electrode 504, left atrial pacing therapy using at least a left atrial ring electrode 506, and shocking therapy using at least a left atrial coil electrode 508.

The ICTD 102 is also shown in electrical communication with the patient's heart 106 by way of an implantable right ventricular lead 108(3) having, in this implementation, a right ventricular tip electrode 510, a right ventricular ring electrode 512, a right ventricular (RV) coil electrode 514, and an SVC coil electrode 516. Typically, the right ventricular lead 108(3) is transvenously inserted into the heart 102 to place the right ventricular tip electrode 510 in the right ventricular apex so that the RV coil electrode 514 will be positioned in the right ventricle and the SVC coil electrode 516 will be positioned in the superior vena cava. Accordingly, the right ventricular lead 108(3) is capable of receiving cardiac signals, and delivering stimulation in the form of pacing and shock therapy to the right ventricle.

Figure 6:
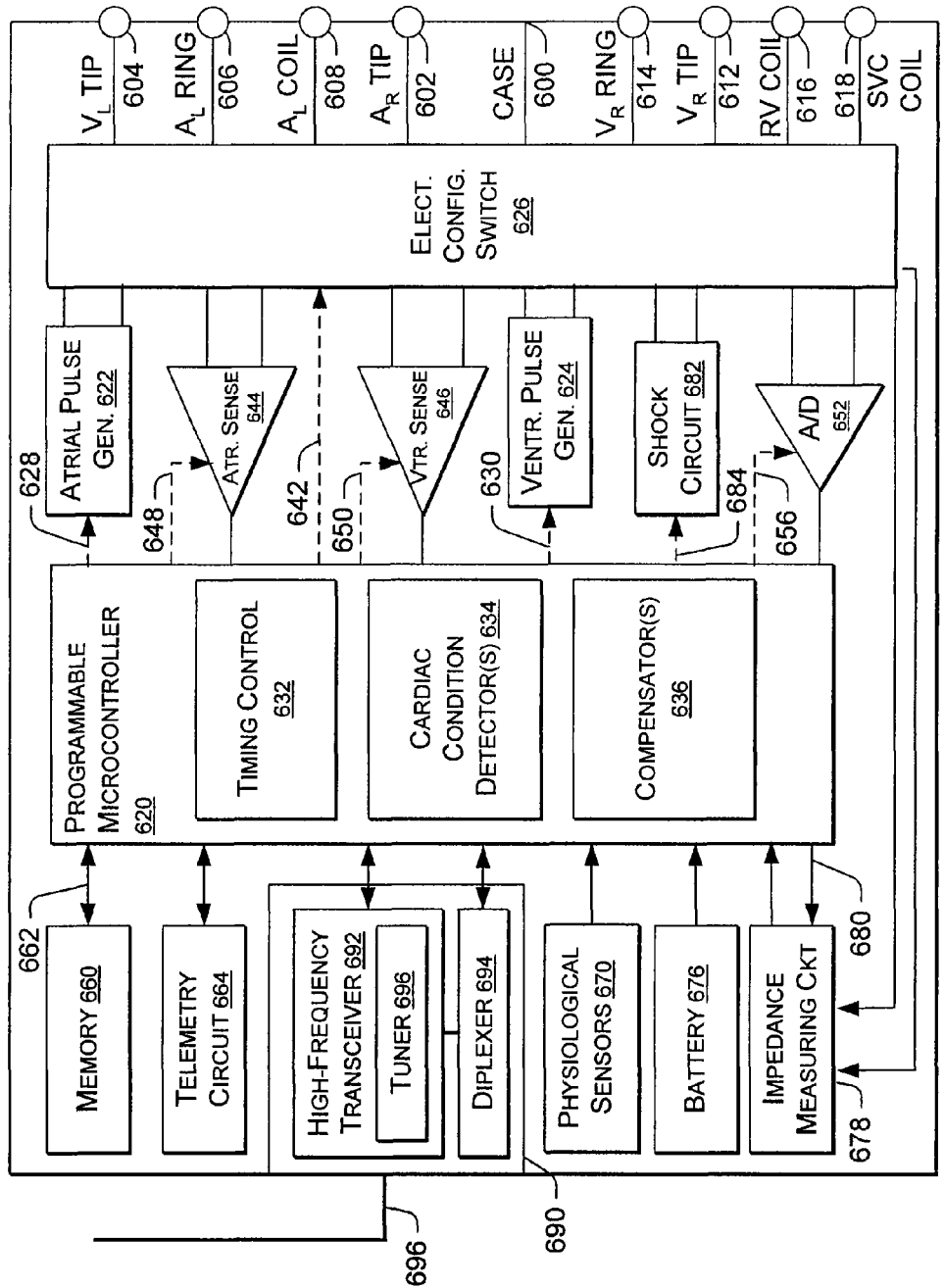
FIG. 6 is a functional block diagram of an exemplary implantable cardiac therapy device.

FIG. 6 shows an exemplary, simplified block diagram depicting various components of the ICTD 102. The ICTD 102 can be configured to perform one or more of a variety of functions including, for example, monitoring heart activity, monitoring patient activity, and treating fast and slow arrhythmias with stimulation therapy that includes cardioversion, defibrillation, and pacing stimulation. While a particular multi-chamber device is shown, it is to be appreciated and understood that this is done for illustration purposes.

The circuitry is housed in housing 600, which is often referred to as the "can", "case", "encasing", or "case electrode", and may be programmably selected to act as the return electrode for unipolar modes. Housing 600 may further be used as a return electrode alone or in combination with one or more of the coil electrodes for shocking purposes. Housing 600 further includes a connector (not shown) having a plurality of terminals 602, 604, 606, 608, 612, 614, 616, and 618 (shown schematically and, for convenience, the names of the electrodes to which they are connected are shown next to the terminals).

To achieve right atrial sensing and pacing, the connector includes at least a right atrial tip terminal ($A_R$ TIP) 602 adapted for connection to the atrial tip electrode 502. To achieve left chamber sensing, pacing, and shocking, the connector includes at least a left ventricular tip terminal ($V_L$ TIP) 604, a left atrial ring terminal ($A_L$ RING) 606, and a left atrial shocking terminal ($A_L$ COIL) 608, which are adapted for connection to the left ventricular ring electrode 504, the left atrial ring electrode 506, and the left atrial coil electrode 508, respectively. To support right chamber sensing, pacing, and shocking, the connector includes a right ventricular tip terminal ($V_R$ TIP) 612, a right ventricular ring terminal ($V_R$ RING) 614, a right ventricular shocking terminal (RV COIL) 616, and an SVC shocking terminal (SVC COIL) 618, which are adapted for connection to the right ventricular tip electrode 510, right ventricular ring electrode 512, the RV coil electrode 514, and the SVC coil electrode 516, respectively.

At the core of the ICTD 102 is a programmable microcontroller 620 that controls various operations of the ICTD, including cardiac monitoring and stimulation therapy. Microcontroller 620 includes a microprocessor (or equivalent control circuitry), RAM and/or ROM memory, logic and timing circuitry, state machine circuitry, and I/O circuitry. Microcontroller 620 includes the ability to process or monitor input signals (data) as controlled by a program code stored in a designated block of memory. Any suitable microcontroller 620 may be used. The use of microprocessor-based control circuits for performing timing and data analysis functions are well known in the art.

For discussion purposes, microcontroller 620 is illustrated as including timing control circuitry 632 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and so on. Microcontroller 220 may further include various types of cardiac condition detectors 634 (e.g., an arrhythmia detector, a morphology detector, etc.) and various types of compensators 636 (e.g., orthostatic compensator, syncope response module, etc.). These components can be utilized by the device 102 for determining desirable times to administer various therapies. The components 632-636 may be implemented in hardware as part of the microcontroller 620, or as software/firmware instructions programmed into the device and executed on the microcontroller 620 during certain modes of operation.

The ICTD 102 further includes an atrial pulse generator 622 and a ventricular pulse generator 624 that generate pacing stimulation pulses for delivery by the right atrial lead 108(1), the coronary sinus lead 108(2), and/or the right ventricular lead 108(3) via an electrode configuration switch 626. It is understood that in order to provide stimulation therapy in each of the four chambers of the heart, the atrial and ventricular pulse generators, 622 and 624, may include dedicated, independent pulse generators, multiplexed pulse generators, or shared pulse generators. The pulse generators 622 and 624 are controlled by the microcontroller 620 via appropriate control signals 628 and 630, respectively, to trigger or inhibit the stimulation pulses.

The electronic configuration switch 626 includes a plurality of switches for connecting the desired electrodes to the appropriate I/O circuits, thereby providing complete electrode programmability. Accordingly, switch 626, in response to a control signal 642 from the microcontroller 620, determines the polarity of the stimulation pulses (e.g., unipolar, bipolar, combipolar, etc.) by selectively closing the appropriate combination of switches (not shown).

Atrial sensing circuits 644 and ventricular sensing circuits 646 may also be selectively coupled to the right atrial lead 108(1), coronary sinus lead 108(2), and the right ventricular lead 108(3), through the switch 626 to detect the presence of cardiac activity in each of the four chambers of the heart. Accordingly, the atrial (ATR. SENSE) and ventricular (VTR. SENSE) sensing circuits, 644 and 646, may include dedicated sense amplifiers, multiplexed amplifiers, or shared amplifiers. Each sensing circuit 644 and 646 may further employ one or more low power, precision amplifiers with programmable gain and/or automatic gain control, bandpass filtering, and a threshold detection circuit to selectively sense the cardiac signal of interest. The automatic gain control enables the ICTD 102 to deal effectively with the difficult problem of sensing the low amplitude signal characteristics of atrial or ventricular fibrillation. Switch 626 determines the "sensing polarity" of the cardiac signal by selectively closing the appropriate switches. In this way, the clinician may program the sensing polarity independent of the stimulation polarity.

The outputs of the atrial and ventricular sensing circuits 644 and 646 are connected to the microcontroller 620 which, in turn, is able to trigger or inhibit the atrial and ventricular pulse generators 622 and 624, respectively, in a demand fashion in response to the absence or presence of cardiac activity in the appropriate chambers of the heart. The sensing circuits 644 and 646 receive control signals over signal lines 648 and 650 from the microcontroller 620 for purposes of controlling the gain, threshold, polarization charge removal circuitry (not shown), and the timing of any blocking circuitry (not shown) coupled to the inputs of the sensing circuits 644 and 646.

Cardiac signals are also applied to inputs of an analog-to-digital (ND) data acquisition system 652. The data acquisition system 652 is configured to acquire intracardiac electrogram signals, convert the raw analog data into a digital signal, and store the digital signals for later processing and/or telemetric transmission to an external device 654. The data acquisition system 652 is coupled to the right atrial lead 108(1), the coronary sinus lead 108(2), and the right ventricular lead 108(3) through the switch 626 to sample cardiac signals across any pair of desired electrodes.

The data acquisition system 652 may be coupled to the microcontroller 620, or other detection circuitry, to detect an evoked response from the heart 106 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 620 detects a depolarization signal during a window following a stimulation pulse, the presence of which indicates that capture has occurred. The microcontroller 620 enables capture detection by triggering the ventricular pulse generator 624 to generate a stimulation pulse, starting a capture detection window using the timing control circuitry 632 within the microcontroller 620, and enabling the data acquisition system 652 via control signal 656 to sample the cardiac signal that falls in the capture detection window and, based on the amplitude, determines if capture has occurred.

The microcontroller 620 is further coupled to a memory 660 by a suitable data/address bus 662, wherein the programmable operating parameters used by the microcontroller 620 are stored and modified, as required, in order to customize the operation of the implantable device 102 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 106 within each respective tier of therapy. With memory 660, the ICTD 102 is able to sense and store a relatively large amount of data (e.g., from the data acquisition system 652), which may transmitted to the external network of knowledge workers for subsequent analysis.

Operating parameters of the ICTD 102 may be non-invasively programmed into the memory 660 through a telemetry circuit 664 in telemetric communication with an external device, such as a programmer 110 or local transceiver 112. The telemetry circuit 664 advantageously allows intracardiac electrograms and status information relating to the operation of the device 102 (as contained in the microcontroller 620 or memory 660) to be sent to the external devices.

The ICTD 100 can further include one or more physiologic sensors 670, commonly referred to as "rate-responsive" sensors because they are typically used to adjust pacing stimulation rate according to the exercise state of the patient. However, the physiological sensor 670 may further be used to detect changes in cardiac output, changes in the physiological condition of the heart, or diurnal changes in activity (e.g., detecting sleep and wake states, detecting position or postural changes, etc.). Accordingly, the microcontroller 620 responds by adjusting the various pacing parameters (such as rate, AV Delay, V-V Delay, etc.) at which the atrial and ventricular pulse generators, 622 and 624, generate stimulation pulses. While shown as being included within the device 102, it is to be understood that the physiologic sensor 670 may also be external to the device 102, yet still be implanted within or carried by the patient. Examples of physiologic sensors that may be implemented in device 102 include known sensors that, for example, sense respiration rate and/or minute ventilation, pH of blood, ventricular gradient, and so forth.

The ICTD 102 additionally includes a battery 676 that provides operating power to all of circuits shown in FIG. 2. If the device 102 is configured to deliver pacing or shocking therapy, the battery 676 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 676 also desirably has a predictable discharge characteristic so that elective replacement time can be detected. As one example, the device 102 employs lithium/silver vanadium oxide batteries.

The ICTD 102 can further include magnet detection circuitry (not shown), coupled to the microcontroller 620, to detect when a magnet is placed over the device 102. A magnet may be used by a clinician to perform various test functions of the device 102 and/or to signal the microcontroller 620 that the external programmer is in place to receive or transmit data to the microcontroller 620 through the telemetry circuits 664.

The ICTD 102 further includes an impedance measuring circuit 678 that is enabled by the microcontroller 620 via a control signal 680. Uses for an impedance measuring circuit 678 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 678 is advantageously coupled to the switch 626 so that any desired electrode may be used.

In the case where the device 102 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 620 further controls a voltage delivery circuit or shock circuit 682 by way of a control signal 684. The shocking circuit 682 generates shocking pulses of low (up to 0.5 Joules), moderate (0.5-10 Joules), or high energy (11 to 40 Joules), as controlled by the microcontroller 620. Such shocking pulses are applied to the patient's heart 106 through at least two shocking electrodes, and as shown in this implementation, selected from the left atrial coil electrode 508, the RV coil electrode 514, and/or the SVC coil electrode 516. As noted above, the housing 600 may act as an active electrode in combination with the RV coil electrode 514, or as part of a split electrical vector using the SVC coil electrode 516 or the left atrial coil electrode 508 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 620 is capable of controlling the synchronous or asynchronous delivery of the shocking pulses.

The ICTD 102 is further designed with the ability to support high-frequency wireless communication, typically in the radio frequency (RF) range. The ICTD 102 is equipped with a high-frequency transceiver 692 and a diplexer 694. High-frequency signals received by a dedicated antenna 696, or via leads 108, are passed to the transceiver 692 directly, or via diplexer 694. The high-frequency transceiver 692 may be configured to operate on one or a few frequencies. Alternatively, the transceiver 692 may include a tuner 696 that tunes to various frequencies when attempting to establish communication links with the external communication device (e.g., programmer, local transceiver, etc.).

In one implementation, the high-frequency circuitry may be contained within a secondary, isolated casing 690 to enable handling of high-frequency signals in isolation from the cardiac therapy circuitry. In this manner, the high-frequency signals can be safely received and transmitted, thereby improving telemetry communication, without adversely disrupting operation of the other device circuitry.

Exemplary Computing Device

Figure 7:
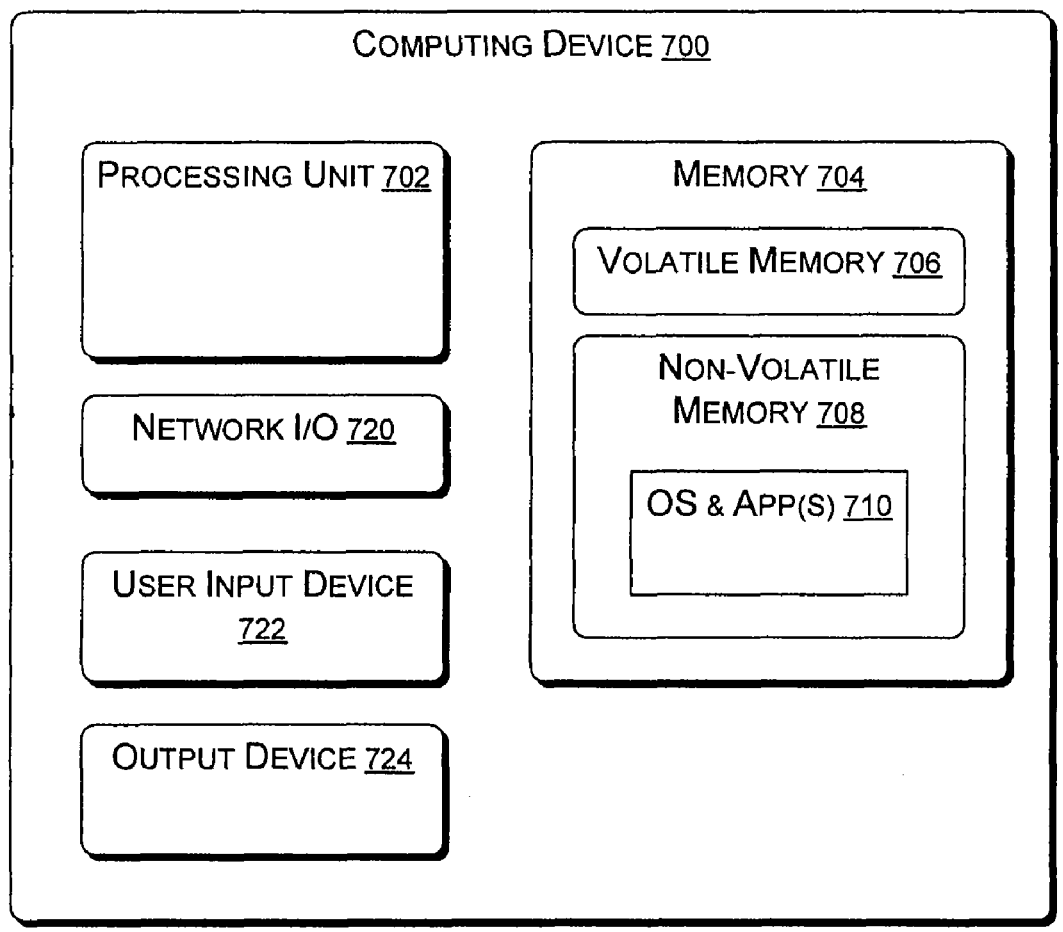
FIG. 7 is a functional block diagram of an exemplary computing device that may be used in the computing systems of the cardiac therapy network architecture.

FIG. 7 shows an exemplary computing device 700 employed in the computing systems of the cardiac therapy network architecture 100. It includes a processing unit 702 and memory 704. Memory 704 includes both volatile memory 706 (e.g., RAM) and non-volatile memory 708 (e.g., ROM, EEPROM, Flash, disk, optical discs, persistent storage, etc.). An operating system and various application programs 710 are stored in non-volatile memory 708. When a program is running, various instructions are loaded into volatile memory 706 and executed by processing unit 702. Examples of possible applications that may be stored and executed on the computing device include the knowledge worker specific applications 206 shown in FIG. 2.

The computing device 700 may further be equipped with a network I/O connection 720 to facilitate communication with a network. The network I/O 720 may be a wire-based connection (e.g., network card, modem, etc.) or a wireless connection (e.g., RF transceiver, Bluetooth device, etc.). The computing device 700 may also include a user input device 722 (e.g., keyboard, mouse, stylus, touch pad, touch screen, voice recognition system, etc.) and an output device 724 (e.g., monitor, LCD, speaker, printer, etc.).

Various aspects of the methods and systems described throughout this disclosure may be implemented in computer software or firmware as computer-executable instructions. When executed, these instructions direct the computing device (alone, or in concert with other computing devices of the system) to perform various functions and tasks that enable the cardiac therapy network architecture 100.

Communication Protocol

One feature of the network architecture is an improved transmission range between the ICTD 102 and an external device such as the offline programmer 110, the local transceiver 112, and/or programmer 116. Long range telemetry allows communication with implanted medical devices at distances greater than conventional "wand telemetry" of a few inches. Longer range telemetry is made possible by employing high-frequency signals, such as RF signals. However, longer range telemetry introduces a challenge regarding how to establish communication with one or more ICTDs 102 at distances larger than several inches.

To address this challenge, the network architecture contemplates a technique for interrogating one or more ICTDs that might be within range of an external device for purposes of establishing a communication link. Once established, the devices can use the link to exchange data and download programming parameters. The interrogation and communication links are conducted over more than one allocated frequency band to support communication with multiple implantable devices.

Figure 8:
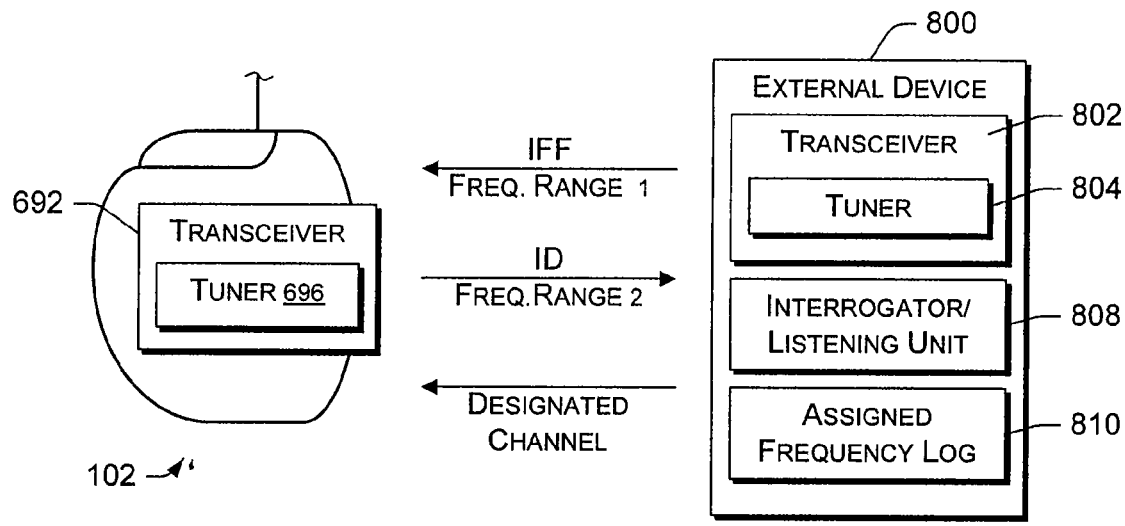
FIG. 8 is a function block diagram of the ICTD and an external communication device to illustrate how the ICTD and communication device establish a communication link.

FIG. 8 shows an exemplary ICTD 102 and an external communication device 800 to illustrate how the communication device 800 interrogates an ICTD 102 to establish a communication link. The external device 800 is equipped with a transceiver 802 that is capable of sending and receiving signals over a wide range of frequencies, such as broadband RF signals. A tuner 804 is provided to tune to these different frequencies. The external communication device 800 may be implemented in any number of ways, including as a programmer 110, as a local transceiver 112, and so on.

The external device 800 is equipped with an interrogation/listening unit 808. It generates an interrogation signal (designated as "IFF" in FIG. 8) designed to invite any listening ICTDs to establish a communication link. The interrogation/listening unit 808 directs the tuner 804 to one or more frequencies within a set of possible interrogating frequencies. At each frequency, the transceiver 802 dispatches the interrogation signal.

The ICTD-based transceiver 692 listens for the interrogation signal. In one implementation, the ICTD transceiver 692 is designed to listen at one frequency within the possible range of interrogating frequencies, although more sophisticated transceivers may be configured to listen over a range of frequencies. When the ICTD receives the interrogation signal, the ICTD-based transceiver 692 transmits a reply at a response frequency within a set of possible response frequencies. The reply may be in the form of a device identification code (designated as "ID" in FIG. 8), or some other message. The reply may be transmitted at a pre-selected frequency or at any one of numerous frequencies within the set of response frequencies. The set of interrogating frequencies and the set of response frequencies may overlap or be mutually exclusive.

The interrogation/listening unit 808 listens for the reply from the ICTD transceiver 692 over the response frequencies. The unit 808 listens for a predetermined response time interval triggered by transmission of the interrogation signal. If no reply is detected within the time interval, the interrogation/listening unit 808 retransmits the interrogation signal and restarts the interval. On the other hand, when the unit 808 detects a reply, it commands the ICTD to tune to a designated frequency channel to facilitate ongoing communication between the ICTD 102 and the external device 800. The frequency assigned to the ICTD is listed in the assigned frequency record 810 and associated with the ICTD. Upon receiving this command, the ICTD-based tuner 696 tunes the transceiver 692 to the designated channel.

From this point, the ICTD and external device can channel hop to other frequencies. According to one aspect, the ICTD and external device are configured to channel hop among frequencies more than once during communication of information (e.g., one segment or bit of information). The channel hopping confers the advantage of greater tolerance to externally-generated electromagnetic interference. This is based on the assumption that interference is less likely to occur in separated frequency bands than in one continuous band. Each information symbol may be encoded as two separated frequencies to take advantage of the decreased probability of interference.

Figure 9:
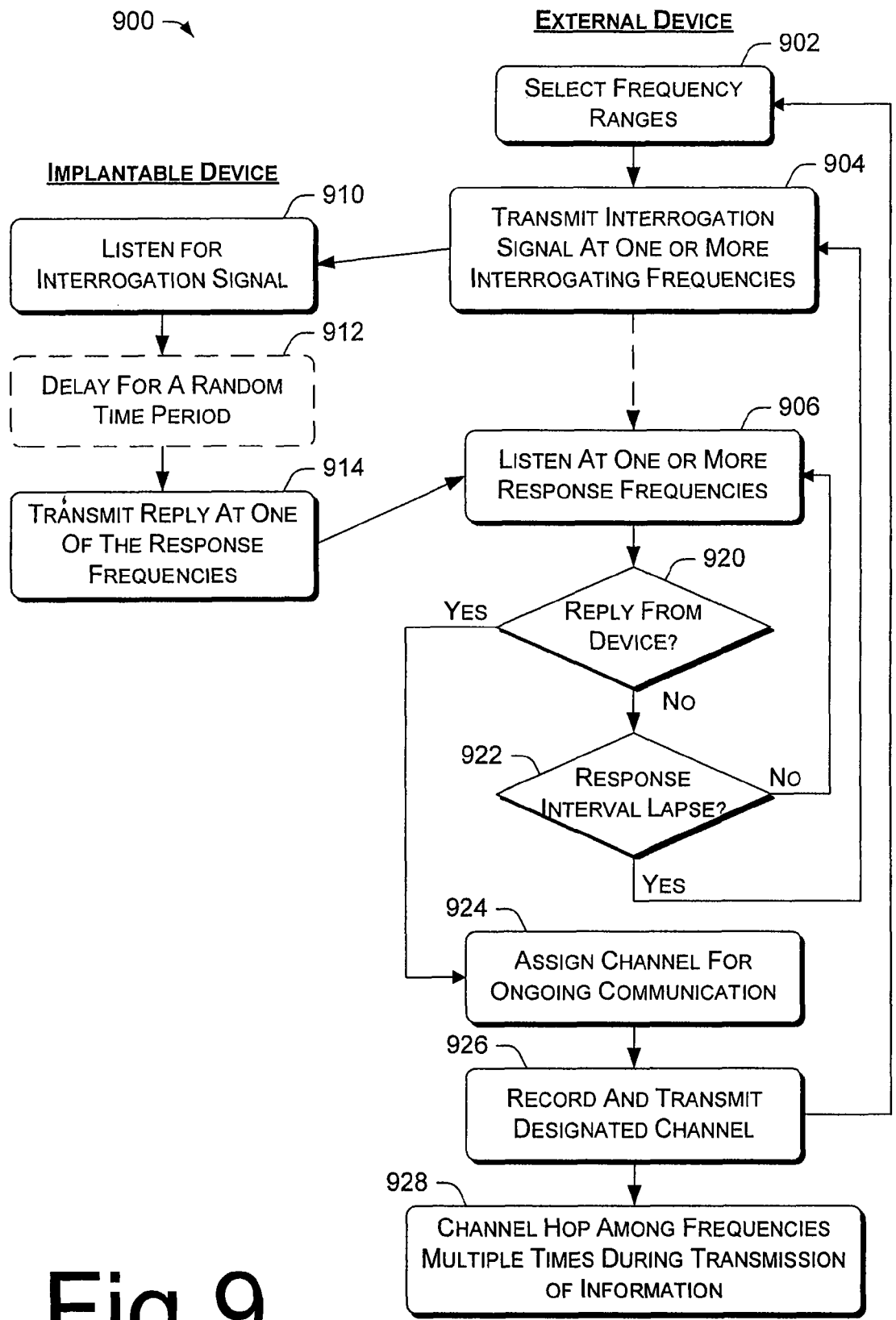
FIG. 9 is a flow diagram of a method for establishing a communication link between the ICTD and the external communication device.

FIG. 9 shows a process 900 for establishing a communication link between the ICTD 102 and the external device 800. Aspects of this process may be implemented in hardware, firmware, or software, or a combination thereof. The process 900 is accomplished by operations performed at the ICTD 102 and the external device 800. To illustrate which devices perform which operations, the various operations are depicted as blocks arranged beneath headings identifying the devices that generally perform the operations.

At block 902, the external device 800 selects frequency ranges for transmitting and receiving signals used in establishment of communication with the ICTD. The selected transmission range encompasses an interrogating frequency to which the ICTD 102 is tuned to receive any interrogation signal from the external device 800. The selected receiving range of frequencies includes a response frequency at which the ICTD 102 is expected to return a reply to the interrogation signal. The transmission and receiving ranges may cover the same frequencies, or overlap so that common frequencies are used in both transmission and reception, or be mutually exclusive bands of frequencies with no common frequency.

At block 904, the interrogation/listening unit 808 directs transceiver 802 to transmit the interrogation code IFF at one or more of the interrogating frequencies. According to one possible implementation, the transceiver 802 transmits the interrogation signal on multiple or all interrogating frequencies, either randomly or in a prescribed order. The external device 800 then begins listening to one or more response frequencies for a reply from the ICTD 102 (block 906). It listens for a predetermined response time interval.

Meanwhile, at block 910, the ICTD 102 is listening at one or more frequencies for the interrogation code. Depending upon power resources, the listening may be continuous or intermittent. Once the interrogation code is detected, the ICTD 102 optionally delays for a random time period within the response time interval (block 912) and then transmits a reply at one of the response frequencies (block 914). The random delay allows the external device to listen for multiple ICTDs. That is, if multiple ICTDs respond to the same interrogation code on the same response frequency, the random delays separate the replies allowing them to be received at the external device 800. The replies may be in the form of device identification codes so that the external device can identify the one or more ICTDs.

The external device 800 listens for any reply over one or more receiving frequencies for a predetermined response time interval (blocks 906, 920, 922). If no reply is received, the external device continues listening until the response interval lapses (i.e., the loop including block 906, the "no" branch from block 920, and the "no" branch from block 922). If no reply is received within the response interval, the external device 902 retransmits the interrogation code (i.e., the "yes" branch from block 922 to block 904).

If a reply is received within the response interval (i.e., the "yes" branch from block 920), the external device 800 assigns a communication channel to the ICTD 102 (block 924). The external device 800 records the channel in the log 810 in association with the specific ICTD, and transmits the designated channel to the ICTD (block 926). The ICTD and external device employ the designated channel for ongoing communication.

Once a particular ICTD and external device are communicating on the assigned channel, that communication channel may be used to download data from the ICTD, query the ICTD, or submit programming instructions to the ICTD. The communicating devices may conduct all continuing communication on the assigned channel, or hop to other frequencies using known frequency hopping techniques. Accordingly, at block 928, the ICTD and external device may optionally channel hop to multiple frequencies multiple times during communication of information.

At this point, the process flow returns to block 902 to select the same or a new set of frequencies with the intention of interrogating and establishing communication with another ICTD.

Figure 10:
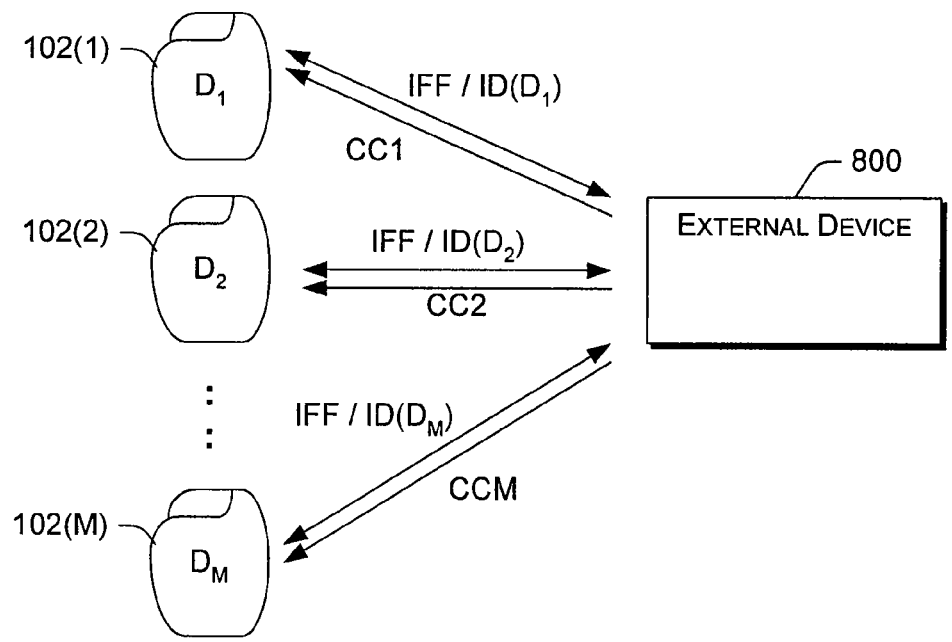
FIG. 10 is a diagrammatic illustration of a system with multiple ICTDs communicating with a common external communication device.

FIG. 10 illustrates the communication protocol for establishing links between the external device 800 and multiple ICTDs 102(1), 102(2), . . . , 102(M). The external device 800 transmits an interrogation code IFF over one or more interrogating frequencies. The ICTDs 102(1)-(M) are tuned or configured to listen to the same or different ones of these interrogating frequencies. When an ICTD receives the interrogation code, it returns a reply on a different frequency being monitored by the external device 800. The reply includes an identification code ID that uniquely identifies the implantable device $D_1, D_2, \ldots, D_M$.

The ICTDs 102(1)-(M) can be configured to transmit the replies after a random delay period. For instance, ICTD 102 (1) might reply at random time $t_1$, which is within the response time interval $T_0$ (i.e., $0<t_1<T_0$). Similarly, ICTDs 102(2), . . . , 102(M) reply at random times $t_2, t_M$, which are likely to be different from one another, but still fall within the response time interval $T_o$. In this manner, if multiple ICTDs listen to the same frequency and respond to the same interrogation code, there is an increased probability that the ICTDs will reply at different times so that the external device receives all replies.

As the external device 800 receives the replies, it assigns different communication channels to the ICTDs 102(1)-(M). For instance, channel CC1 is assigned for communication between ICTD 102(1) and the external device 800; channel CC2 is assigned for communication between the ICTD 102 (2) and the external device 800; and channel CCM is assigned for communication between ICTD 102(M) and the external device 800.

The assigned communication channels are recorded in the log 810 in association with the ICTDs identification codes so that continuing communication between the ICTDs and the external devices are handled in a one-to-one link. This ensures that data read from individual ICTDs are associated with the appropriate patients and any programming instructions are delivered to the appropriate ICTDs, thereby preventing any situation where one ICTD is programmed to deliver therapy intended for another patient.

Exemplary Packaging Design

Figure 11:
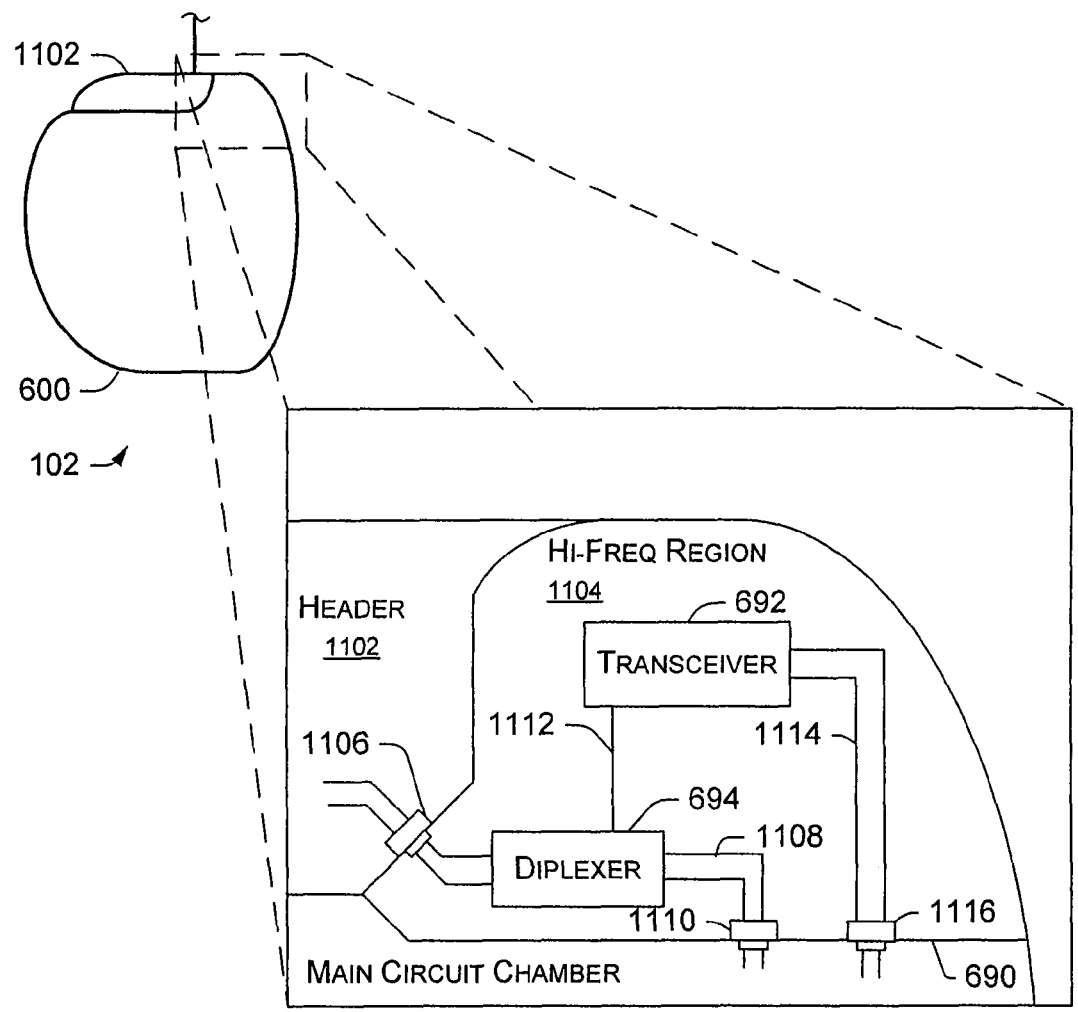
FIG. 11 is a diagrammatic illustration of an ICTD with packaging that defines dual isolated chambers, one for housing high-frequency circuitry and a second for housing the ICTD monitoring and stimulation circuitry.

FIG. 11 shows an exemplary ICTD 102 that is equipped with additional high-frequency packaging and circuitry to support long range telemetry. Generally, ICTD 102 is designed with a hermetically shielded can 600 to prevent electromagnetic interference (EMI) from disrupting operation of the sensing and/or stimulation circuitry. The can 600 employs one or more filters to block high-frequency transmissions (e.g., radio frequencies) and other sources of EMI (e.g., automobile engines). As an example, the filters typically attenuate signals significantly, above 1 MHz. Thus, the can 600 prevents penetration of high frequencies and tries to limit communication to the low frequency ranges of less than 200 KHz.

The ICTD 102 has a header 1102 that holds the connection terminals for leads 108(1)-(3). The header is commonly formed of an epoxy material mounted on can 600, which is commonly formed of a conducting material such as titanium. In this construction, the high-frequency circuitry is contained within a separate frequency-isolated packaging region 1104 adjacent to the header 1102. The region 1104 is defined in part by wall 690, which is constructed, for example, of a conducting material such as titanium. The high-frequency packaging region 1104 can be thought of as a separate can or chamber that isolates the RF components from the main circuitry. The dual-can design enables the ICTD to handle high-frequency signals carrying data and control information in one can of the device without disrupting operation of the main circuitry in the second can or chamber of the device.

The transceiver 692 and diplexer 694 are positioned within the high-frequency packaging region 1104. Signals received from a lead 108 or a dedicated antenna 696 are passed through an unfiltered feed-through 1106 to a diplexer 694. The diplexer 694 allows two signals of different frequencies to be transmitted along the same conductor and separates the signal frequencies onto two different connections. In the illustrated implementation, the diplexer 694 is designed to direct RF signals to the RF transceiver 692 and the electrocardiograph (ECG) signals to the main circuitry in the main chamber.

The diplexer's first connection 1108 leads to a feed-through 1110 into the ICTD circuitry within the main chamber. The diplexer 694 filters this first connection to pass low frequencies of the ECG signal. High frequencies are blocked and therefore do not interfere with the sensing of the ECG.

A second connection 1112 on the diplexer 694 connects to the transceiver 692. The filter on this connection is tuned to pass a band of high frequencies. The transceiver is capable of receiving and transmitting high-frequency signals, such as those found in the radio frequency range. As one example range, the transceiver handles signals within 200 to 900 MHz. Low frequency signals, such as the ECG, on connection 1112 are blocked. The transceiver 692 extracts any codes, data and/or control instructions from the carrier frequency modulation and passes the information to the ICTD circuitry via connections 1114 and a feed-through 1116. The feed-through 1116 can be filtered to prevent any high-frequency components from entering the main circuit chamber. The metal shield encompassing the high-frequency chamber 1104 blocks spurious signals emanating from the RF transceiver 692 from interfering with the sensing and pacing functions of the main circuitry. Power is supplied to the transceiver 692 and diplexer 694 from the battery in the main circuitry chamber via the feed-throughs 1110 and 1116.

The dual-chamber design provides optimal isolation. With the diplexer, dual enclosure regions, and filtered feed-throughs, the design isolates the main monitoring/stimulating circuitry from RF interference emanating from the diplexer or transceiver, while simultaneously allowing long-range RF telemetry communication. Additionally, the design allows the leads to be used as both stimulation/sensing leads and as a radio frequency (RF) antenna, without causing interference to the monitoring and/or stimulation functions.

In the illustrated implementation, the high-frequency region 1104 is shown adjacent to header 1102 and above the main circuit chamber, encapsulated by the outer can wall of the device and the interior wall 690. It is noted that the region 1104 may be located in any number of places. It may be, for example, implemented as an isolated cavity contained entirely within the main circuit chamber. Alternatively, it may be constructed external to the ICTD 102, but employ part of the exterior can 600 to define a portion of the region. Another possible implementation is to construct the high-frequency region as a separate implantable can that is in communication with the ICTD, but implanted apart from the ICTD 102.

The antenna for transmitting and receiving the high-frequency data signals may be implemented in a number of ways. One approach is to use one or more of the leads 108 (1)-(3) as the antenna. Another approach is to employ a dedicated antenna positioned within the header region 1102. A third approach is to employ a dedicated antenna that extends beyond the header region 1102. Still another approach is to integrate the antenna into the can 600.

CONCLUSION

Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:

1. A method comprising:
receiving data from an implantable medical device at a data integrator configured to accumulate the data;
storing the data in a central repository communicatively connected to the data integrator;
evaluating the data for accuracy and completeness at a processing system commutatively connected to the central repository;
processing the data according to a knowledge worker specific application that is specifically tailored to place the data into condition for a first knowledge worker;
transmitting at least a portion of the data from the central repository to a distribution/presentation system configured to serve the data according to protocols and formats of a computer system at a first location associated with a first knowledge worker;
transmitting the data from the distribution/presentation system to the first location according to the protocols and formats of the computer system at the first location;
further processing the data at the first location by the computer system, the further processing specific to a use of the data by the first knowledge worker;
generating at the first location additional data that is useful to at least one of a patient associated with the implantable medical device or a second knowledge worker; and
transmitting the additional data from the first location to a second location associated with the second knowledge worker.

2. A method as recited in claim 1, and further comprising generating a notification to the patient associated with the implantable medical device in response to the processing of the data.

3. The method of claim 2, wherein the generating the notification is performed by the second knowledge worker.

4. The method of claim 1, and further comprising generating a notification from the first location to the second location in response to the processing of the data.

5. The method of claim 1 wherein transmitting the processed data comprises transmitting the processed data directly from the first location to the second location.

6. The method of claim 1, wherein transmitting the processed data comprises transmitting the processed data from the first location to the second location through the central repository.

7. The method of claim 1, wherein the first knowledge worker comprises a clinical group, the second knowledge worker comprises a healthcare provider, and the processing the data at the first location comprises identifying data for inclusion in patient populations that can be studied and analyzed.

8. The method of claim 1, wherein the first knowledge worker comprises a manufacture of the implantable medical device, the portion of the data comprises data pertaining to operation of the implantable medical device, and the additional data comprises data useful to develop better technologies for future generations of implantable medical devices.

9. A system comprising:
means for receiving data from an implantable medical device and storing it in a central repository;
means for evaluating the accuracy and completeness of the data;
means for generating at least two different data packages, each data package comprising different portions of the data;
means for transmitting at least a first data package from the central repository to a first location associated with a first knowledge worker, the first data package served to a computer system at the first location according to protocols and formats desired by the computer system;
means for processing the first data package at the first location by a computer system, the processing specific to a use of the first data package by the first knowledge worker;
means for generating, at the first location, additional data that is useful to at least one of a patient associated with the implantable medical device or a second knowledge worker; and
means for transmitting the additional data from the first location to a second location associated with the second knowledge worker.

10. The system of claim 9, and further comprising means for generating a notification to the patient associated with the implantable medical device in response to the processing of the data.

11. The system of claim 10, wherein the means for generating a notification comprises means for generating the notification by the second knowledge worker.

12. The system of claim 9, and further comprising means for generating a notification from the first location to the second location in response to the processing of the data.

13. The system of claim 9, wherein the means for transmitting the processed data comprises means for transmitting the processed data directly from the first location to the second location.

14. The system of claim 9, wherein the means for transmitting the processed data comprises means for transmitting the processed data from the first location to the second location through the central repository.

15. The system of claim 9, wherein the first knowledge worker comprises a clinical group, the second knowledge worker comprises a healthcare provider, and the processing the data at the first location comprises identifying data for inclusion in patient populations that can be studied and analyzed.

16. The system of claim 9, wherein the first knowledge worker comprises a clinical scientist, the data package includes heart data but does not include patient identification information, and the additional data comprises the data useful to gain a better understanding of how implantable medical devices operate in general.

17. A method comprising:
receiving data from an implantable medical device at a central repository;
processing the data by a processing system in communication with the central repository according to a knowledge worker specific application that is specifically tailored to create a data package that includes a portion of the data which is of interest to a first knowledge worker;
storing the data package in the central repository;
transmitting the data package from the central repository to a distribution/presentation system in communication with the central repository;
serving the data package from the distribution/presentation system to a first location associated with the first knowledge worker according to protocols and formats of a computer system at the first location;
performing further processing of the data package at the first location to obtain data results and to generate instructions corresponding to the data results; and
transmitting the instructions from the first location to a second location associated with a second knowledge worker.

18. The method of claim 17, and further comprising generating a notification from the first location to the second location in response to the processing of the data.

19. The method of claim 17, wherein transmitting the processed data comprises transmitting the processed data directly from the first location to the second location.

20. The method of claim 17, wherein transmitting the processed data comprises transmitting the processed data from the first location to the second location through the central repository.

21. The method of claim 17, wherein the first knowledge worker comprises a clinical group, the second knowledge worker comprises a healthcare provider, and the instructions comprises instructions to include or exclude a patient in a patient population that can be studied and analyzed.

22. The method of claim 17, wherein the first knowledge worker comprises a health-care worker, the portion of the data includes electrocardiogram data (ECG) and patient identification information for a patient in which the implantable medical device is implanted, and the instructions comprise an improved therapy for the patient.

* * * * *